United States Patent

Lee et al.

[11] Patent Number: 5,153,223
[45] Date of Patent: Oct. 6, 1992

[54] BIURETS, AMINOCARBONYL CARBAMATES, AND AMINOCARBONYL THIOCARBAMATES USEFUL AS ACAT INHIBITORS

[75] Inventors: Helen T. Lee, Ann Arbor; Joseph A. Picard; Drago R. Sliskovic, both of Ypsilanti, all of Mich.

[73] Assignee: Warner-Lambert Company, Morris Plains, N.J.

[21] Appl. No.: 690,750

[22] Filed: Apr. 24, 1991

[51] Int. Cl.$^5$ .................. A61K 31/175; C07C 275/62
[52] U.S. Cl. ............................. 514/591; 514/231.8; 514/254; 514/330; 514/428; 514/522; 514/564; 514/539; 514/237.5; 544/168; 544/391; 546/226; 548/567; 558/417; 560/21; 562/439; 564/38
[58] Field of Search .................. 564/38; 514/591, 522, 514/539, 564; 558/417; 560/21; 562/439

[56] References Cited

U.S. PATENT DOCUMENTS

| | | | |
|---|---|---|---|
| 3,305,549 | 2/1967 | Chubb et al. | 260/247.2 |
| 3,407,193 | 10/1968 | McColl et al. | 260/239 |
| 4,371,544 | 2/1983 | Fujimura et al. | 514/591 |

FOREIGN PATENT DOCUMENTS

T026784 12/1980 Hungary .
8152859 3/1982 Japan .
8177959 4/1982 Japan .
2055042 3/1980 United Kingdom .
2055043 3/1980 United Kingdom .

OTHER PUBLICATIONS

Hoffmann, CA 58, 2387h (abstract only).

Primary Examiner—Richard L. Raymond
Assistant Examiner—Shailendra Kumar
Attorney, Agent, or Firm—Ruth H. Newtson

[57] ABSTRACT

Novel compounds useful as ACAT inhibitors having the formula

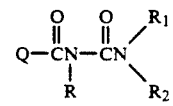

wherein Q is $R_5O$; $R_5S—$ or $NR_3R_4$; wherein R is hydrogen or alkyl $C_1-C_{20}$ or $—CH_2Ph$; wherein $R_1$, $R_2$, $R_3$ and $R_4$ are hydrogen, a hydrocarbon chain aralkyl, phenyl or substituted phenyl or form a heterocyclic ring; wherein $R_5$ is phenyl or substituted phenyl, naphthyl or substituted naphthyl, a hydrocarbon chain or aralkyl.

6 Claims, No Drawings

BIURETS, AMINOCARBONYL CARBAMATES, AND AMINOCARBONYL THIOCARBAMATES USEFUL AS ACAT INHIBITORS

BACKGROUND OF INVENTION

This invention relates to chemical compounds having pharmacological activity, to pharmaceutical compositions which include these compounds, and to a pharmaceutical method of treatment. More particularly, this invention concerns certain biurets and aminocarbonyl carbamates which inhibit the enzyme acyl coenzyme A:cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which are more selective in their action: that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acylCoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides compounds of the following general Formula I, methods of using said compounds and pharmaceutical compositions comprising said compounds:

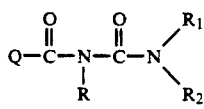

Formula I wherein R is hydrogen, a straight or branched alkyl $C_1$–$C_{20}$ or —$CH_2Ph$ wherein Ph is phenyl and is unsubstituted or is substituted with from 1 to 3 substituents selected from straight or branched alkyl having from 1 to 6 carbon atoms, straight or branched, alkoxy having from 1 to 6 carbon atoms, chlorine, bromine, fluorine, or iodine; wherein each of $R_1$ and $R_2$ is selected from:

(a) hydrogen (b) the group

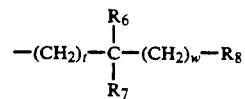

wherein t is zero to 4; w is zero to 4 with the proviso that the sum of t and w is not greater than 5; $R_6$ and $R_7$ are independently selected from hydrogen or alkyl having from 1 to 6 carbon atoms, or when $R_6$ is hydrogen, $R_7$ can be selected from the groups defined for $R_8$; and $R_8$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_q$—$NR_9R_{10}$ wherein $R_9$ and $R_{10}$ are independently hydrogen or alkyl of from 1 to 4 carbon atoms, and q is zero or one;

(c) a straight or branched hydrocarbon chain having from 1 to 20 carbon atoms and which is saturated or contains from 1 to 3 double bonds;

(d) an alkyl group having from 1 to 6 carbon atoms wherein the terminal carbon is substituted with hydroxy, —$NR_9R_{10}$ wherein $R_9$ and $R_{10}$ have the meanings defined above, or —COOalkyl wherein alkyl is straight or branched and has from 1 to 4 carbon atoms;

(e) phenyl or phenyl substituted with from 1 to 3 substituents selected from straight or branched alkyl having from 1 to 6 carbon atoms, alkoxy which is straight or branched and has from 1 to 6 carbon atoms, alkylthio which is straight or branched and has from 1 to 6 carbon atoms, —$(CH_2)_q$—$NR_9R_{10}$ wherein $R_9$ and $R_{10}$ and q have the meanings defined above, hydroxy, nitro, cyano, chlorine, fluorine, bromine, or trifluoromethyl; or (f) $NR_1R_2$ taken together form a monocyclic heterocyclic group selected from pyrrolidino, piperidino, morpholino, or piperazino, each of which is unsubstituted or is substituted with one substituent selected from straight or branched alkyl having from 1 to 6 carbon atoms, phenyl, benzyl, or substituted phenyl or substituted benzyl wherein the substituents vary from 1 to 3 and can be on any position of 2 through 6 of the aromatic ring and are selected from straight or branched alkyl having from 1 to 4 carbon atoms, straight or branched alkoxy having from 1 to 4 carbon atoms, hydroxy, fluorine, chlorine, bromine, trifluoromethyl, cyano, or nitro, or $NR_1R_2$ taken together form a phenothiazine or a dibenzoazepine ring system; wherein Q is —$NR_3R_4$, —$OR_5$, or —$SR_5$ wherein each of $R_3$ and $R_4$ has the meaning defined above for $R_1$ and $R_2$, and wherein $R_5$ is selected from:

(a) phenyl which is unsubstituted or is substituted with from one to three substituents selected from: phenyl, alkyl having from one to six carbon atoms and which is straight or branched, alkoxy having from one to six carbon atoms and which is straight or branched, phenoxy, hydroxy, fluorine, chlorine, bromine, cyano, nitro, trifluoromethyl,

—COOH,

—COOalkyl wherein alkyl has from one to four carbon atoms and which is straight or branched, —$(CH_2)_q NR_9 R_{10}$ wherein q, $R_9$ and $R_{10}$ have the meanings defined above;

(b) 1- or 2 naphthyl which is unsubstituted or substituted with one to three substituents selected from phenyl, alkyl having from one to six carbon atoms and which is straight or branched, alkoxy having from one to six carbon atoms and which is straight or branched, hydroxy, phenoxy, fluorine, chlorine, bromine, cyano, nitro, trifluoromethyl

—COOH,

—COOalkyl wherein alkyl has from one to four carbon atoms and is straight or branched, —$(CH_2)_q NR_9 R_{10}$ wherein q, $R_9$, and $R_{10}$ have the meanings defined above;

(c) the group

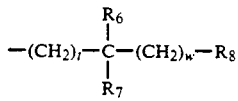

wherein t, w, $R_6$, $R_7$ and $R_8$ have the meanings defined above; and (d) a straight or branched hydrocarbon chain having from 1 to 20 carbon atoms and which is saturated or contains from one to three double bonds; or a pharmaceutically acceptable salt thereof with the provisos (i) that at least one of $R_1$ and $R_2$ and one of $R_3$ and $R_4$ is other than hydrogen; (ii) that when both of $R_1$ and $R_2$ or when both of $R_3$ and $R_4$ are the group

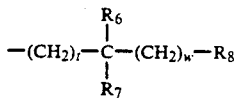

$R_7$ is hydrogen or alkyl.

DETAILED DESCRIPTION OF INVENTION

The compounds of Formula I provide a class of biurets and aminocarbonyl carbamates which are ACAT inhibitors rendering them useful in treating hypercholesterolemia and atherosclerosis. The biurets of this invention may be depicted by the following general Formula II, the aminocarbonyl carbamates may be depicted by the following general Formula III, and the aminocarbonyl thiocarbamates may be depicted by the following general Formula IV:

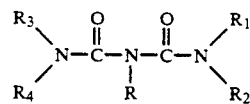 Formula II

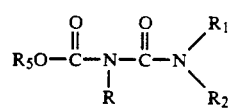 Formula III

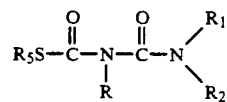 Formula IV

In the above general Formulas II, III, and IV the various substituents R, $R_1$, $R_2$, $R_3$, $R_4$ and $R_5$ have the meanings defined in Formula I.

In the compounds of the present invention illustrative examples of straight or branched saturated hydrocarbon chains or alkyl having from 1 to 20 carbon atoms include methyl, ethyl, n-propyl, isopropyl, n-butyl, isobutyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 50heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, tert-butyl, and pentyloxy.

The term alkylthio having from 1 to 6 carbon atoms means the group $C_{1-6}$alkyl-S— wherein the alkyl moiety is straight or branched.

Preferred compounds of this invention are those of Formula II and III wherein one of $R_1$ and $R_2$ is hydrogen and more preferred are compounds wherein the other of $R_1$ and $R_2$ is substituted phenyl. More preferably in the compounds of Formula II one of $R_1$ and $R_2$ is 2,6-disubstituted phenyl and the other of $R_1$ and $R_2$ is hydrogen. Also, more preferred in the compounds of Formula III are those wherein one of $R_1$ and $R_2$ is hydrogen, the other is 2,6-disubstituted phenyl and $R_5$ is a straight or branched saturated hydrocarbon chain having from 1 to 20 carbon atoms.

Pharmaceutically acceptable salts of the compounds of Formula I, II, III, and IV are also included as a part of the present invention.

The base salts may be generated from compounds of Formulas I, II, and III by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, *J Pharm Sciences* 66:1-19 (1977).

Suitable acids for forming acid salts of the compounds of Formulas I, II, and III which contain a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Example | IAI $IC_{50}$ ($\mu M$) |
| --- | --- |
| 1 | 0.6 |
| 2 | >1 |
| 3 | >5 |
| 4 | 1.04 |
| 5 | 0.34 |
| 6 | 0.35 |
| 7 | 0.25 |
| 8 | 0.89 |
| 9 | >5 |
| 10 | >5 |
| 11 | 0.75 |
| 12 | 1.9 |
| 13 | 3.5 |
| 14 | 1.7 |
| 15 | 0.98 |
| 16 | 7.8 |

TABLE 1-continued

| Example | IAI $IC_{50}$ ($\mu M$) |
| --- | --- |
| 17 | 0.065 |
| 18 | 0.12 |
| 19 | 0.35 |
| 20 | 0.39 |
| 21 | 1.06 |
| 22 | 0.75 |
| 23 | 6.8 |
| 24 | 0.046 |
| 25 | >1 |
| 26 | 0.17 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The norma chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. Compounds were dosed at 30 mg/kg unless otherwise noted. The results of this trial for representative compounds of the present invention appear in Table 2.

TABLE 2

| Compound of Example | % Change in Plasma TC Values (mg/dL) |
| --- | --- |
| 1 | −9 |
| 4 | −13* |
| 5 | −40* |
| 6 | −5* |
| 7 | −23* |
| 8 | −18* |
| 11 | −27* |
| 12 | −19* |
| 14 | −8 |
| 15 | −9 |
| 17 | −14 |
| 18 | −38 |
| 19 | −26 |
| 20 | −24 |
| 21 | −22 |
| 22 | −22 |
| 23 | −26 |
| 24 | −33 |
| 25 | No change |

*Dosed at 50 mg/kg

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets. Pharmaceutical compositions of the compounds of general Formula I are prepared by procedures well known in the art.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of this invention are prepared by various means. The compounds of Formula II wherein R is hydrogen can be prepared according to the following reaction scheme wherein $R_1$, $R_2$, $R_3$ and $R_4$ have the meanings defined in Formula.

A solution of an amine (a) in an appropriate solvent, such as, diethyl ether, dichloromethane or tetrahydrofuran is added dropwise to a solution of chlorocarbonyl isocyanate in a similar solvent, at 0° or less (−78° to 0° C.). The resulting solution is stirred for 1 to 6 hours. A solution of a second amine ($R_3R_4NH$) and an acid scavenger such as triethylamine or pyridine in an appropriate solvent is added dropwise. The resulting mixture is warmed to room temperature and let stand for 2 to 24 hours. The reaction is partitioned between an appropriate organic solvent and an aqueous acid wash (1N HCl, 5% citric acid, etc). The organics are dried with an appropriate drying agent such as $MgSO_4$ or $Na_2SO_4$ and concentrated to give crude product. Chromatography gives the desired product. The compounds of Formula II wherein R is an alkyl group of from 1 to 20 carbon atoms or —$CH_2Ph$ are prepared from the compound of formula (c) by treatment with DBU (1,8-diazabicyclo[5,4,0]undec-7-ene) and an alkyliodide or an appropriate benzyl iodide by procedures well known in the art.

The compounds of Formula II may also be prepared according to the following reaction scheme wherein

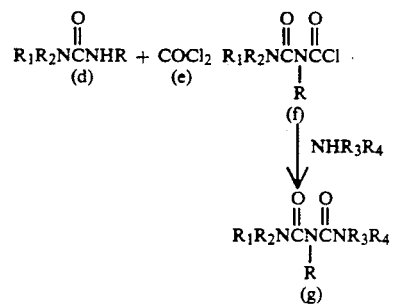

phosgene (e) in an appropriate solvent, such as, toluene, or benzene is added to a solution of the urea (d) in a solvent such as diethyl ether, tetrahydrofuran or dichloromethane. Upon completion of the reaction and removal of the excess phosgene the residue containing (f) is redissolved in, e.g., tetrahydrofuran and the amine $NHR_3R_4$ is added. The reaction mixture is stirred at room temperature for from 6 to 24 hours to give the product (g). The urea (d) is prepared by reaction of an isocyanate of the formula $R_1R_2NCO$ and an amine $NH_2R$ by means well known in the art.

The compounds of Formula III and IV wherein R is hydrogen may be prepared as depicted below wherein X is oxygen or sulfur:

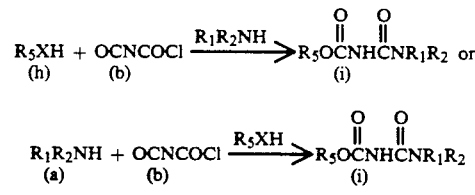

A solution of the first nucleophile ($R_5XH$ or $R_1R_2NH$) in an appropriate solvent such as diethyl ether, dichloromethane or tetrahydrofuran is added dropwise to a cold (<0° C.) solution of chlorocarbonyl isocyanate in a similar solvent. The resulting solution is aged (¼ to 6 hours) before a solution of the second nucleophile ($R_1R_2NH$ or $R_5XH$) and an acid scavenger such as triethylamine or pyridone in an appropriate solvent such as diethyl ether, dichloromethane or tetrahydrofuran is added dropwise. The resulting mixture is warmed to room temperature and aged (¼ to 16 hours). The reaction is then partitioned between an organic solvent and an acidic aqueous solution (e.g., 1N HCl, 5% citric acid). The organic layer is dried and concentrated to give a crude product mixture. Chromatography then gives the desired product.

The compounds of Formula III and IV wherein R is alkyl of from 1 to 20 carbon atoms or —CH$_2$Ph are prepared from the compounds of formula (i) by treatment with DBU and an alkyliodide or an appropriate benzyliodide by well known procedures.

The various alcohols, amines and ureas depicted above in the reaction schemes are commercially available or can be prepared by means well known in the art.

The following specific examples further illustrate the invention.

EXAMPLE 1

N'-[2,6-bis(1-methylethyl)phenyl]-2-methyl-N,N-diphenyliminodicarbonic diamide

Phosgene (in toluene, 10 mmol, 7.92 mL) was added to a solution of N-methyl-N',N'-diphenylurea (10 mmol, 2.26 g) in 20 mL THF at room temperature. The mixture was stirred at room temperature for 2 days and then 60° C. for 2 weeks. The solvent and excess phosgene were removed under vacuum. The residue was redissolved in 20 mL of THF and 2,6-diisopropylaniline (20 mmol, 3.55 g) was added all at once. A white precipitate appeared, and the mixture was stirred at room temperature overnight. The solvent was removed and 50 mL of EtOAC was added to the residue. The mixture was filtered and the filtrate was concentrated under vacuum. The product was isolated by chromatography (hexane: EtOAc=8:1). The oil weighed 2.6 g (65%). IHNMRdata for Example 1.
δ 1.1~1.4 (M,12H); 2.87 (S. 3H)
3.09~3.29 (M,2H); 3.45 (S. 1H)
6.9~7.5 (M,13H)

EXAMPLE 2

N-[2,6-bis(1-methylethyl)phenyl)-N'-(diphenylmethyl) iminodicarbonic amide

A solution of 2,6-diisopropylaniline (1.5 g, 8.5 mmol) in 50 mL Et$_2$O was added dropwise to a solution of chlorocarbonyl isocyanate (0.68 mL, 8.5 mmol) in 40 mL Et$_2$O at −50° C. under an atmosphere of N$_2$. The resulting solution was stirred for 3 hours, allowing the temperature to rise to −30° C. A solution of benzhydrylamine (1.46 mL, 8.5 mmol) and excess triethylamine (1.0 mL) in 50 mL Et$_2$O was added dropwise. The resulting suspension was warmed to room temperature and stirred for 16 hours. The reaction was partitioned between EtOAc and 1N HCl. The organic layer was dried over MgSO$_4$, filtered, and evaporated to give a white foam. Chromatography (SiO$_2$, 10% EtOAc/hexanes) gave 0.86 g (23%) of the title compound as a white solid, M.P. 139° to 141° C.

When in the procedure of Example 2 an appropriate amount of the amine listed below was substituted for benzhydrylamine and the general procedure of Example 2 was followed the respective products listed below were obtained.

| Example | Amine | Product |
|---|---|---|
| 3 | 2,6-bis(1-methylethyl)phenylamine | N,N'-bis[2,6-bis(1-methylethyl)phenyl]imidodicarbonic diamide, m.p. 222-224° C. |
| 4 | dibenzylamine | N'-[2,6-bis(1-methylethyl)-phenyl]-N,N-bis(phenylmethyl)imidodicarbonic diamide, m.p. 163-166° C. |
| 5 | diphenylamine | N'-[2,6-bis(1-methylethyl)-phenyl]-N,N-diphenylimidodicarbonic diamide, m.p. 135-139° C. |
| 6 | dioctylamine | N-[2,6-bis(1-methylethyl)phenyl]-N,N-dioctylimidodicarbonic diamide, m.p. 44–48° C. |
| 7 | dibutylamine | N'-[2,6-bis(1-methylethyl)phenyl]-N,N-dibutylimidodicarbonic diamide, m.p. 112-114°C. |
| 8 | 5H-dibenz-[b,f]azepine | N-[[[2,6-bis(1-methylethyl)phenyl]amino]carbonyl]-10,11-dihydro-5H-dibenz[b,f]azepin-5-carboxamide, m.p. 178-179° C. |
| 9 | pyrrolidine | N-[[[2,6-bis(1-methylethyl)phenyl]amino]carbonyl]-1-pyrrolidinecarboxamide, m.p. 175-177° C. |
| 10 | diethylamine | N'-[2,6-bis(1-methylethyl)phenyl]-N,N-diethylimidodicarbonic diamide; m.p. 160-163° C. |
| 11 | (1-methylethyl)(benzyl)amine | N'-[2,6-bis(1-methylethyl)phenyl]-N-(1-methylethyl)-N-(phenylmethyl)imidodicarbonic diamide, m.p. 92-95° C. |
| 12 | phenothiazine | N-[[[2,6-bis(1-methylethyl)phenyl]amino]carbonyl]-10H-phenothiazine-10-carboxamide, m.p. 176-177° C. |
| 13 | 4-phenylpiperidine | N-[[[2,6-bis(1-methylethyl)phenyl]amino]carbonyl]-1-[(4-phenyl)piperidine]carboxamide, m.p. 205-207°C. |
| 14 | (methyl)(tetradecyl)amine | N'-[2,6-bis(1-methylethyl)phenyl]-N-methyl-N-tetradecylimidodicarbonic diamide, m.p. 47-49° C. |

EXAMPLE 15

[[[2,6-bis(1-methylethyl)phenyl]amino]carbonyl] carbamic acid,2,6-bis(1-methylethyl)phenyl ester A solution of 2,6-diisopropylphenol (1.69 g, 9.5 mmol) in 50 mL Et$_2$O was added dropwise to a solution of chlorocarbonyl isocyanate (0.76 mL, 9.5 mmol) in 50 mL Et$_2$O at −50° C. under an atmosphere of N$_2$. The temperature was raised to 0° C. over 2 hours. A solution of 2,6-diisopropylaniline (1.68 g, 9.5 mmol) and excess triethylamine (1 mL) in 50 mL Et$_2$O was added dropwise to the reaction. The resulting mixture was stirred at room temperature for 16 hours. Partitioned between 1N HCl and EtOAc. The organic layer was dried (MgSO$_4$), filtered, and concentrated to give a white solid. Chromatography (10% EtOAc/hexanes) gave the title compound (1.50 g, 37%), M.P. 184°-186° C.

When in the procedure of Example 15 an appropriate amount of the alcohol listed below was substituted for 2,6-diisopropylphenol and the general procedure of Example 15 was followed the respective products listed below were obtained.

| Example | Alcohol | Product |
|---|---|---|
| 16 | benzhydrol | [[[2,6-bis(1-methylethyl)phenyl]amino]carbonyl] carbamic acid, diphenylmethyl ester, m.p. 169-172° C. |
| 17 | 1,1-dimethyltridecanol | [[[2,6-bis(1-methylethyl)phenyl]amino]carbonyl]carbamic acid, 1,1-dimethyltridecyl ester, m.p. 65-67° C. |
| 18 | dodecanol | [[[2,6-bis(1-methylethyl) |

-continued

| Example | Alcohol | Product |
|---|---|---|
| | | phenyl]amino]carbonyl] carbamic acid, dodecyl ester, m.p. 100–102° C. |
| 19 | 1-methyl-undecanol | (±)[[[2,6-bis(1-methylethyl) phenyl]amino]carbonyl] carbamic acid, 1-methylundecyl ester, m.p. 59–61° C. |
| 20 | 1-methyl-octanol | (±)[[[2,6-bis(1-methylethyl) phenyl]amino]carbonyl] carbamic acid, 1-methyloctyl ester, m.p. 100–102° C. |
| 21 | 1-methyl-hexanol | (±)[[[2,6-bis(1-methylethyl) phenyl]amino]carbonyl] carbamic acid, 1-methylhexyl ester, m.p. 113–115° C. |
| 22 | 1-methyl-nonanol | (±)[[[2,6-bis(1-methylethyl) phenyl]amino]carbonyl] carbamic acid, 1-methylnonyl ester, m.p. 84–86° C. |
| 23 | 1-methyl-pentadecanol | (±)[[[2,6-bis(1-methylethyl) phenyl]amino]carbonyl] carbamic acid, 1-methylpentadecyl ester, m.p. 68–70° C. |
| 24 | 1-methyl-tridecanol | (±)[[[2,6-bis(1-methylethyl) phenyl]amino]carbonyl] carbamic acid, 1-methyltridecyl ester, m.p. 65–66° C. |

When in the procedure of Example 15 an appropriate amount of the amine listed below was substituted for 2,6-diisopropylaniline and the general procedure of Example 15 was followed the respective products listed below were obtained.

| Example | Amine | Product |
|---|---|---|
| 25 | benzhydryl-amine | [[(diphenylmethyl)amino]carbonyl]carbamic acid, 2,6-bis(1-methylethyl)phenyl ester, m.p. 174–176° C. |
| 26 | diphenylamine | [(diphenylamino)carbonyl]carbamic acid, 2,6-bis(1-methylethyl)phenyl ester, m.p. 142–146° C. |

When in the procedure of Example 15 an appropriate amount of dodecanethiol or 1-methyltridecanethiol is substituted for 2,6-diisopropylphenol the following compounds are obtained:

[[[2,6-bis(1-methylethyl)phenyl]amino]carbonyl] thiocarbamic acid, dodecyl ester;

[[[2,6-bis(1-methylethyl)phenyl]amino]caronyl] thiocarbamic acid, 1-methyltridecyl ester.

We claim:

1. A compound having the formula

wherein

R is hydrogen, a straight or branched alkyl $C_1$–$C_{20}$; or $CH_2Ph$ wherein Ph is phenyl and is unsubstituted or is substituted with from 1 to 3 substituted selected from straight or branched alkyl having from 1 to 6 carbon atoms, straight or branched alkoxy having from 1 to 6 carbon atoms, chlorine, bromine, fluorine, or iodine;

wherein $R_1$ is hydrogen and $R_2$ is 2,6-bis(1-methylethyl)phenyl);

wherein each of $R_3$ and $R_4$ is selected from:

(a) hydrogen,
(b) the group

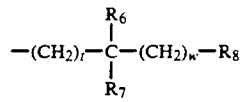

where t is zero to 4; w is zero to 4 with the proviso that the sum of t and w is not greater than 5; $R_6$ and $R_7$ are independently selected from hydrogen or alkyl having from 1 to 6 carbon atoms, or when $R_6$ is hydrogen, $R_7$ can be selected from the groups defined from $R_8$; and $R_8$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, cyano, trifluoromethyl, —COOH, COOalkyl wherein alkyl has from 1 to 4 carbon atoms, or —$(CH_2)_q$—$NR_9R_{10}$ where $R_9$ and $R_{10}$ are independently hydrogen or alkyl of from 1 to 4 carbon atoms, and q is zero or one;

(c) a straight or branched hydrocarbon chain having from 1 to 20 carbon atoms and which is saturated or contains from 1 to 3 double bonds;

(d) an alkyl group having from 1 to 6 carbon atoms wherein the terminal carbon is substituted with hydroxy, —$NR_9R_{10}$ wherein $R_9$ and $R_{10}$ have the meanings defined above, or —COOalkyl wherein alkyl is straight or branched and has from 1 to 4 carbon atoms; or (e) phenyl or phenyl substituted with from 1 to 3 substitutents selected from straight or branched alkyl having from 1 to 6 carbon atoms, alkoxy which is straight or branched and has from 1 to 6 carbon atoms, alkylthio which is straight or branched and has from 1 to 6 carbon atoms, —$(CH_2)_q$—$NR_9R_{10}$ wherein $R_9$ and $R_{10}$ and q have the meanings defined above, hydroxy, nitro, cyano, chlorine, fluorine, bromine, or trifluoromethyl.

2. A compound of claim 1 wherein $R_3$ and $R_4$ are a straight or branched hydrocarbon chain having from 1 to 20 carbon atoms and which is saturated or contains from 1 to 3 double bonds.

3. A compound of claim 2 which is N-[2,6-bis(1-methylethyl)phenyl]-N,N-dioctylimido-dicarbonic diamide; N'-[2,6-bis(1-methylethyl)phenyl]-N,N-dibutylimido-dicarbonic diamide; N'-[2,6-bis(1-methylethyl)phenyl]-N,N-diethylimido-dicarbonic diamide; N'-[2,6-(1-methylethyl)phenyl]-N-methyl-N-tetradecylimidodicarbonic diamide.

4. A pharmaceutical composition which comprises a compound of claim 1 and a pharmaceutically useful carrier.

5. A method of treating atherosclerosis in a patient in need thereof which comprises administering to said patient an effective amount of a compound of claim 1 in combination with a pharmaceutically acceptable carrier.

6. A compound of claim 1 which is N'-[2,6-bis(1-methylethyl)phenyl]-2-methyl-N,N-diphenyliminodicarbonic diamide; N-[2,6-bis(1-methylethyl) phenyl]-N'-(diphenylmethyl)iminodicarbonic amide; N,N'-bis[2,6-bis(1-methylethyl)phenyl]imidodicarbonic diamide; N'-[2,6-bis(1-methylethyl) phenyl]-N,N-bis(phenylmethyl)imidodicarbonic diamide; N'-[2,6-bis(1-methylethyl)phenyl]-N,N-di-phenylimidodicarbonic diamide; N'-[2,6-bis(1-methylethyl)phenyl]-N-(phenylmethyl) imidodicarbonic diamide.

* * * * *

UNITED STATES PATENT AND TRADEMARK OFFICE
CERTIFICATE OF CORRECTION

PATENT NO. : 5,153,223

DATED : October 6, 1992

INVENTOR(S) : Lee, et al

It is certified that error appears in the above-indentified patent and that said Letters Patent is hereby corrected as shown below:

Column 11, line 62, "1 to 3 substituted" should read "1 to 3 substituents".

Column 12, line 9, "where" should be "wherein".

Column 12, line 13, "from $R_8$" should be "for $R_8$".

Column 12, line 21, "where" should be "wherein".

Column 12, line 33, "substitutents" should be "substituents".

Column 12, line 49, "N'-[2,6-(1- ..." should be "N'-[2,6-bis(1- ...".

Signed and Sealed this

Twelfth Day of October, 1993

*Attest:*

BRUCE LEHMAN

*Attesting Officer*     *Commissioner of Patents and Trademarks*